United States Patent
Carbajal Navarro et al.

(10) Patent No.: US 8,993,521 B2
(45) Date of Patent: Mar. 31, 2015

(54) ORAL PHARMACEUTICAL COMPOSITION OF DESMOPRESSIN

(75) Inventors: Nuria Carbajal Navarro, Barcelona (ES); Antonio Boix Montanes, Barcelona (ES); Carlos Nieto Abad, Barcelona (ES); Antonio Parente Duena, Barcelona (ES); Ricard Mis Vizcaino, Barcelona (ES); Cesar Garcia Plumed, Barcelona (ES)

(73) Assignees: GP Pharm, S.A., Barcelona (ES); Laboratorio Reig Jofre, S.A., Barcelona (ES)

( * ) Notice: Subject to any disclaimer, the term of this patent is extended or adjusted under 35 U.S.C. 154(b) by 694 days.

(21) Appl. No.: 12/672,255

(22) PCT Filed: Aug. 1, 2008

(86) PCT No.: PCT/ES2008/000539
§ 371 (c)(1),
(2), (4) Date: Apr. 27, 2010

(87) PCT Pub. No.: WO2009/027561
PCT Pub. Date: Mar. 5, 2009

(65) Prior Publication Data
US 2011/0251123 A1    Oct. 13, 2011

(30) Foreign Application Priority Data
Aug. 6, 2007    (ES) .................... 200702215

(51) Int. Cl.
A61K 38/11    (2006.01)
A61K 38/22    (2006.01)
C07K 14/575    (2006.01)
A61K 9/00    (2006.01)

(52) U.S. Cl.
CPC ............ *A61K 9/0095* (2013.01); *A61K 9/006* (2013.01); *A61K 38/11* (2013.01)
USPC .......................................... 514/10.9; 514/9.7

(58) Field of Classification Search
USPC .................................................. 514/10.9, 9.7
See application file for complete search history.

(56) References Cited

U.S. PATENT DOCUMENTS

| | | | |
|---|---|---|---|
| 5,298,256 A | 3/1994 | Flockhart et al. | |
| 2003/0119728 A1* | 6/2003 | Scheidl et al. | 514/11 |
| 2003/0216302 A1 | 11/2003 | Bhowmick et al. | |
| 2004/0235956 A1 | 11/2004 | Quay | |

FOREIGN PATENT DOCUMENTS

| | | |
|---|---|---|
| EP | 0163723 B1 | 4/1990 |
| EP | 0517211 A1 | 9/1992 |
| EP | 0381345 B1 | 7/1994 |
| EP | 0689452 B1 | 6/1999 |
| EP | 0752877 B1 | 7/2000 |
| EP | 0710122 B1 | 12/2001 |
| EP | 1473029 A1 | 11/2004 |
| EP | 1500390 A1 | 1/2005 |
| EP | 1501534 B1 | 7/2006 |
| WO | WO 94/03157 A1 | 2/1994 |
| WO | WO 95/01185 A1 | 1/1995 |
| WO | WO 97/48379 A1 | 12/1997 |
| WO | WO 01/60394 A1 | 8/2001 |
| WO | WO 03/097080 A1 | 11/2003 |
| WO | WO 2004/014411 A1 | 2/2004 |
| WO | WO 2004/019910 * | 3/2004 |
| WO | WO 2004/019910 A2 | 3/2004 |
| WO | WO 2005/046707 A1 | 5/2005 |
| WO | WO 2005/089724 | 9/2005 |
| WO | WO 2005/115339 A2 | 12/2005 |

OTHER PUBLICATIONS

International Search Report dated May 27, 2009 issued in corresponding PCT Application No. PCT/ES2008/000539 (8 pages).
International Preliminary Report on Patentability dated Dec. 12, 2009 issued in corresponding PCT Application No. PCT/ES2008/000539 (8 pages).

* cited by examiner

*Primary Examiner* — Gina Justice
*Assistant Examiner* — Genevieve S Alley
(74) *Attorney, Agent, or Firm* — Foley & Lardner, LLP; Benjamin A. Berkowitz

(57) ABSTRACT

The present invention relates to a liquid oral pharmaceutical composition of desmopressin, and its use for the treatment of central diabetes insipidus, primary nocturnal enuresis, bleeding in patients with Hemophilia A, with von Willebrand-Jürgens disease and postoperative bleeding.

9 Claims, No Drawings

ORAL PHARMACEUTICAL COMPOSITION OF DESMOPRESSIN

CROSS-REFERENCE TO RELATED PATENT APPLICATIONS

The application is a National Phase Entry of PCT Application No. PCT/ES2008/000539 filed Aug. 1, 2008, which claims priority to Spanish Patent Application No. P200702215 filed Aug. 6, 2007, including the specification, claims and abstract, incorporated herein by reference in their entirety.

FIELD OF THE INVENTION

The present invention is comprised generally within the biomedicine field and particularly relates to a novel liquid, oral and flexible-dose pharmaceutical composition of desmopressin and its use for the treatment of central diabetes insipidus, primary nocturnal enuresis, bleeding in patients with Hemophilia A, with von Willebrand-Jürgens disease and postoperative bleeding.

BACKGROUND OF THE INVENTION

It has been known for some time that 1-deamino-8-D-arginine-vasopressin, commonly known as desmopressin, has a useful biological effect for the treatment of diabetes insipidus, presents antidiuretic activity and reduces and normalizes the prolonged bleeding time.

Desmopressin has been administered as a drug by different routes, in different presentation forms and in combination with different excipients. By way of example, the administration of desmopressin by nasal, oral, vaginal, rectal, subcutaneous, intravenous and intramuscular route has been described. Oral administration route with gastrointestinal absorption of desmopressin has the problem that the bioavailability is clearly lower than by other administration routes, since desmopressin is degraded by stomach and intestinal enzymes and is metabolized in the liver. The most common alternative administration route of desmopressin, in the form of its acetic salt, is through nasal or oral mucosa, given the convenience of administration through these routes compared to other parenteral administration routes.

Nasal pharmaceutical compositions of desmopressin acetate in the form of drops or spray in which the active substance is absorbed through the mucous membrane are known in the state of the art. For example, document EP 0710122 A1 describes aqueous compositions of desmopressin for nasal administration by means of a spray, stable at room temperature and which compositions contain a buffer, an osmotic pressure-controlling agent and a quaternary amine as a preservative, particularly benzalkonium chloride. An aqueous composition comprising parabens at a concentration of 1 mg/ml as preservatives instead of quaternary amines is also described in the examples.

Document WO 2004/014411 A1 relates to an aqueous composition for nasal administration in the form of drops or spray comprising desmopressin and tris(hydroxymethyl) aminomethane as stabilizer and absorbent. In particular this composition can contain auxiliary agents such as methyl and/or propyl p-hydroxybenzoate.

Likewise, document WO 03/97080 A1 describes an aqueous nasal composition of desmopressin stable at room temperature and in an acceptable support furthermore comprising a pH buffer, a paraben as a preservative and a cosolvent improving the preservative properties of parabens.

Furthermore, document WO 94/03157 A1 relates to a composition for nasal or vaginal administration in the form of liposome dispersion or microemulsion made up of salmon calcitonin, although desmopressin is also cited, and a thermosetting polymer. This composition also contains methylparaben as a preservative.

Documents WO 01/60394 A1 and WO 2004/019910 A2 describe pharmaceutical compositions of desmopressin which are administered orally or nasally by means of spray and which are absorbed through the mucous membrane. In particular, document WO 01/60394 A1 describes an oral, nasal or sublingual composition of desmopressin with malic acid as a buffer of pH 4-6, and at the same time as a preservative, which can additionally contain other preservatives, such as parabens for example. This composition also necessarily contains an osmotic agent and is administered, according to the examples, by means of a nasal or sublingual spray, or syrup. Furthermore, document WO 2004/019910 A2 describes a buccal spray for the administration of active substances through the oral mucosa, in which desmopressin is mentioned as one of the possible antidiuretic active substances.

Document EP 0381345 A1 describes a pharmaceutical composition in aqueous solution form comprising desmopressin and carboxymethyl cellulose and which is administered intranasally in the form of drops or with a sprayer or by means of intramuscular, intravenous or subcutaneous injection.

Likewise, document WO 2005/115339 A2 describes liquid, semi-solid or solid pharmaceutical compositions with a component which increases the absorption of the drug through the oral, nasal, gastrointestinal or vaginal mucosa. In particular, a liquid composition comprising desmopressin as a drug and methylparaben as a preservative and administered through the nasal mucosa, or by gastrointestinal, oral, ocular or vaginal route, is described.

Other oral pharmaceutical compositions of desmopressin in solid dose form are also known in the state of the art. Documents EP 0163723 A1, EP 0689452 A1, EP 752877 A1, EP 1473029 A1, EP 1500390 A1, EP1501534 A1, EP 0517211 A1, WO 2005/089724 A1 and WO 2005/046707 A1 describe different oral compositions in the form of tablets, capsules or powders comprising desmopressin and which compositions are absorbed through the oral mucosa and/or gastrointestinally. However, all these solid formulations have limited dose versatility and are complex to administer for populations having difficulty swallowing.

Finally, buccal patches containing desmopressin are additionally known. Document U.S. Pat. No. 5,298,256 A describes a pharmaceutical composition containing desmopressin in the form of a buccal patch adhered to the oral mucosa.

The previously cited documents describe compositions of desmopressin which are administered through the oral or sublingual mucosa by means of patches, capsules, tablets or syrups and through the nasal mucosa by means of drops or sprays. However, the nasal administration route presents irritation problems due to osmotic agents of the composition and/or the agents used to increase the absorption, and problems derived from the small area available for the absorption in the nasal cavity. In contrast, oral administration forms known in the state of the art have the drawback of being impersonal, i.e., they have scarce or null flexible-dose which allows treating each patient in an individualized manner, a problem that will be aggravated if, as is the case of desmopressin, the pharmacological activity of the drug is high. In addition, the solid formulations for oral administration of desmopressin of the state of the art are complex to administer for special populations such as the elderly with difficulty in swallowing and for children who do not want to do it.

Therefore, there is still a need to find a presentation form that jointly solves the problems of irritation and capacity of the absorption area presented by the nasal route, and furthermore the lack of flexible-dose and the difficulty of administering for special populations which oral administration forms present. A stable, liquid, flexible-dose pharmaceutical composition for oral administration containing neither osmotic agents nor absorption enhancing agents and comprising a therapeutically effective amount of desmopressin is object of the present invention.

A problem of drugs with peptides, particularly those having sulfur bridges such as desmopressin, is the easy degradation of their aqueous solutions, therefore the presence of preservatives in these solutions is necessary. Among the preservatives known in the state of the art for aqueous compositions of the oxytocin peptide families are parabens or p-hydroxybenzoates.

In addition to the previously mentioned documents which describe compositions containing parabens, document US 2004/0235956 A1 describes liquid compositions of carbetocin for their administration to mucosae in the form of solutions, syrups, suspensions or elixirs. In a particular embodiment the liquid solution of carbetocin comprises parabens as preservatives.

DESCRIPTION OF THE INVENTION

The present invention provides liquid pharmaceutical compositions for oral administration comprising desmopressin, useful for the treatment of central diabetes insipidus, primary nocturnal enuresis, bleeding in patients with Hemophilia A, with von Willebrand-Jürgens disease and postoperative bleeding.

Therefore, a first aspect of the present invention relates to a stable, liquid, flexible-dose pharmaceutical composition for oral administration comprising a therapeutically effective amount of desmopressin and comprising neither osmotic agents nor absorption enhancing agents.

Likewise, the pharmaceutical composition of the present invention does not comprise any pH buffer.

In the present invention "stable" means that the pH of the composition is maintained between 3.5 and 5.0 at least for 12 months at 25° C.

In a particular embodiment, the therapeutically effective amount of desmopressin is administered in the form of one or several of its pharmaceutically acceptable salts, preferably as desmopressin acetate.

The therapeutically effective amount of desmopressin in the composition of the invention is comprised between 0.001 mg/ml and 5 mg/ml; preferably between 0.01 mg/ml and 2 mg/ml and more preferably between 0.1 mg/ml and 1 mg/ml.

In a particular embodiment, the pharmaceutical composition of the present invention additionally comprises one or several pharmaceutically acceptable auxiliary agents selected from the group formed by preservatives, antibacterial and antifungal agents, and acids for adjusting the pH of the composition.

Included among the preservatives, antibacterial and antifungal agents that the pharmaceutical composition of the present invention can comprise are those selected from the group formed by parabens or p-hydroxybenzoates such as, for example and in a non-limiting manner, methylparaben, ethylparaben, propylparaben, butylparaben, isobutylparaben, isopropylparaben, benzylparaben and the like or salts thereof or mixtures of these compounds. In a preferred embodiment, the preservative used in the composition of the present invention is a mixture of methylparaben and propylparaben. The total amount of parabens in the composition of the invention is between 0.1 mg/ml and 4 mg/ml; preferably between 1 mg/ml and 3 mg/ml and more preferably between 1.5 mg/ml and 2.5 mg/ml.

Although the composition of the present invention does not comprise a pH buffer, it is necessary to initially adjust the pH of the composition between 3.5 and 5.0 in order for the composition to be stable. Compounds used for adjusting the pH of the solution between 3.5 and 5.0 are mineral acids, organic acids and/or amino acids such as, for example and in a non-limiting manner, hydrochloric acid, nitric acid, phosphoric acid, sulfuric acid, acetic acid, benzoic acid, citric acid, ascorbic acid, aspartic acid, diatrizoic acid, tartaric acid, lactic acid, hydracrylic acid, glutamic acid, maleic acid, succinic acid, oxalic acid, malic acid, malonic acid, mandelic acid, pyruvic acid or mixtures thereof.

The dose of the composition of the invention which must be administered depends on several factors including age, condition of the patient, pathology, severity of the pathology, dosage form and administration frequency. In any case, both a liquid dosage in the form of drops, and in the form of syrup, has the advantage over oral compositions of desmopressin known in the state of the art of having greater flexibility, which allows more accurately adjusting the dose of desmopressin to the needs of the patient.

The composition object of the present invention can be prepared by any of the methods known in the state of the art. In particular, the composition of the present invention is prepared by means of the mixture of a therapeutically effective amount of desmopressin in an aqueous solution of the preservatives and adjusting the pH to a value between 3.5 and 5.0.

In a particular embodiment, the stable, liquid, flexible-dose pharmaceutical composition is presented in a multidose container in the form of drops for oral administration that are absorbed through the oral and/or sublingual mucosa.

In a particular embodiment, the stable, liquid, flexible-dose pharmaceutical composition is presented in a multidose container in the form of syrup for oral gastrointestinal administration or syrup for oral administration that is absorbed through the oral and/or sublingual mucosa.

In another aspect, the present invention relates to the use of the composition of the invention in the preparation of a medicament for the treatment of central diabetes insipidus, primary nocturnal enuresis, bleeding in patients with Hemophilia A, with von Willebrand-Jürgens disease and postoperative bleeding.

DETAILED DESCRIPTION OF THE INVENTION

The present inventors have surprisingly found a stable, liquid, flexible-dose pharmaceutical composition for oral administration comprising a therapeutically effective amount of desmopressin and comprising neither osmotic agents nor absorption enhancing agents.

EXAMPLES

The present examples intend to illustrate and not limit the invention.

Example 1

Pharmaceutical composition of desmopressin (Table 1).

TABLE 1

| Ingredients | Amount (mg) (mg/ml) |
|---|---|
| Desmopressin acetate | 6 (0.4) |
| Sodium methylparaben | 31.5 (2.1) |
| Sodium propylparaben | 3.3 (0.22) |
| 0.1N hydrochloric acid | q.s. pH 3.5-5.0 |
| Water for injection | q.s. 15 ml |

Example 2

Pharmaceutical composition of desmopressin (table 2).

TABLE 2

| Ingredients | Amount (mg) (mg/ml) |
|---|---|
| Desmopressin acetate | 6 (0.4) |
| Sodium methylparaben | 22.5 (1.5) |
| Sodium butylparaben | 1.5 (0.1) |
| Acetic acid | q.s. pH 3.5-5.0 |
| Water for injection | q.s. 15 ml |

Example 3

Pharmaceutical composition of desmopressin (Table 3).

TABLE 3

| Ingredients | Amount (mg) (mg/ml) |
|---|---|
| Desmopressin acetate | 6 (0.4) |
| Sodium methylparaben | 27 (1.8) |
| Sodium benzylparaben | 1.5 (0.1) |
| Citric acid | q.s. pH 3.5-5.0 |
| Water for injection | q.s. 15 ml |

Example 4

Stability of the pharmaceutical compositions of the previous examples at 25° C.

Stability of the Composition of Example 1

| Assay | Initial | 15 days | 2 months | 3 months | 6 months | 12 months | 18 months |
|---|---|---|---|---|---|---|---|
| pH | 4.40 | 4.41 | 4.44 | 4.52 | 4.56 | 4.51 | 4.56 |
| Desmopressin titration | 99.4% | 100.6% | 100.6% | 99.8% | 100.0% | 98.6% | 98.7% |

Stability of the composition of Example 2

| Assay | Initial | 15 days | 2 months | 3 months | 6 months | 12 months | 18 months |
|---|---|---|---|---|---|---|---|
| pH | 4.80 | 4.82 | 4.83 | 4.88 | 4.90 | 4.91 | 4.93 |
| Desmopressin titration | 99.7% | 99.6% | 99.6% | 99.7% | 99.4% | 98.9% | 98.6% |

Stability of the Composition of Example 3

| Assay | Initial | 15 days | 2 months | 3 months | 6 months | 12 months | 18 months |
|---|---|---|---|---|---|---|---|
| pH | 3.60 | 3.62 | 3.65 | 3.66 | 3.68 | 3.71 | 3.77 |
| Desmopressin titration | 99.8% | 100.2% | 100.0% | 99.8% | 99.7% | 99.3% | 98.9% |

The invention claimed is:

1. A pharmaceutical composition consisting of a therapeutically effective amount of desmopressin or a pharmaceutically acceptable salt thereof, one or several pharmaceutically acceptable auxiliary agents selected from a group consisting of preservatives, antibacterial and antifungal agents, and one or several acids for adjusting the pH of the composition,
   wherein the preservatives, antibacterial and antifungal agents are selected from parabens, salts or mixtures thereof,
   wherein the acids are selected from the group formed by hydrochloric acid, nitric acid, phosphoric acid, sulfuric acid, acetic acid and citric acid, or mixtures thereof,
   said pharmaceutical composition being a stable, liquid and flexible-dose composition in aqueous solution form of pH between 3.5 and 5.0 for oral administration, which comprises neither osmotic agents nor absorption enhancing agents.

2. The pharmaceutical composition according to claim 1, wherein the therapeutically effective amount of desmopressin is administered in the form of desmopressin acetate.

3. The pharmaceutical composition according to claim 1, wherein the therapeutically effective amount of desmopressin is comprised between 0.001 mg/ml and 5 mg/ml.

4. The pharmaceutical composition according to claim 3, wherein the therapeutically effective amount of desmopressin is comprised between 0.01 mg/ml and 2 mg/ml.

5. The pharmaceutical composition according to claim 4, wherein the therapeutically effective amount of desmopressin is comprised between 0.1 mg and 1 mg/ml.

6. The pharmaceutical composition according to claim 1, wherein the parabens are selected from methylparaben, ethylparaben, propylparaben, butylparaben, isobutylparaben, isopropylparaben and benzylparaben.

7. The pharmaceutical composition according to claim 1, wherein the composition is in the form of drops for oral administration which are absorbed through the oral and/or sublingual mucosa.

8. The pharmaceutical composition according to claim 1, wherein the composition is in the form of a syrup for oral gastrointestinal administration or syrup for oral administration which is absorbed through the oral and/or sublingual mucosa.

9. A method of treating a disease or condition selected from central diabetes insipidus, primary nocturnal enuresis, bleeding in patients with Hemophilia A, with von Willebrand-Jürgens disease and postoperative bleeding, which comprises the administration to a subject in need of treatment the pharmaceutical composition according to claim 1.

\* \* \* \* \*